United States Patent
Mohammed

(10) Patent No.: US 7,351,529 B2
(45) Date of Patent: Apr. 1, 2008

(54) METHODS FOR DETECTING GENETIC MOSAICISMS USING ARRAYS

(75) Inventor: Mansoor Mohammed, Houston, TX (US)

(73) Assignee: PerkinElmer LAS, Inc., Waltham, MA (US)

( * ) Notice: Subject to any disclaimer, the term of this patent is extended or adjusted under 35 U.S.C. 154(b) by 957 days.

(21) Appl. No.: 10/260,733

(22) Filed: Sep. 27, 2002

(65) Prior Publication Data

US 2003/0124584 A1    Jul. 3, 2003

Related U.S. Application Data

(60) Provisional application No. 60/325,853, filed on Sep. 27, 2001.

(51) Int. Cl.
*C12Q 1/68* (2006.01)
*C12P 19/34* (2006.01)
*C07H 21/04* (2006.01)

(52) U.S. Cl. .................. 435/6; 435/91.2; 536/24.31; 536/24.32; 536/24.33

(58) Field of Classification Search .................. 435/6; 536/24.31, 26.6, 24.32, 23.1
See application file for complete search history.

(56) References Cited

U.S. PATENT DOCUMENTS

| 6,048,695 | A  | * | 4/2000 | Bradley et al. | 435/6 |
| 6,197,501 | B1 |   | 3/2001 | Cremer et al. | 435/6 |
| 6,251,601 | B1 | * | 6/2001 | Bao et al. | 435/6 |
| 6,261,775 | B1 |   | 7/2001 | Bastian et al. | 435/6 |

FOREIGN PATENT DOCUMENTS

WO    WO 97/18326    5/1997

OTHER PUBLICATIONS

Kuukasjarvi et al. Optimizing DOP-PCR for universal amplification of small DNA samples in comparative genomic hybridization. Gene, Chromosomes & Cancer, vol. 18, pp. 94-101, 1997.*

Supplementary Partial European Search Report for EP 02 76 6404; mailing date: Oct. 4, 2004.

Pollack, et al., "Genome-wide analysis of DNA copy-number changes using cDNA microarrays", *Nature Genetics*, vol. 23, No. 1, pp. 41-46, Sep. 1999.

Cheung, S. W., et al., "Exclusion of chromosomal mosaicism in amniotic fluid cultures: efficacy of in situ versus flask techniques" Prenat Diagn 1990; 10:41-57.

Claussen, U., et al., "Exclusion of chromosomal mosaicism in prenatal diagnosis" Hum Genet 1984; 67:23-28.

Hook, E. B., "Exclusion of chromosomal mosaicism: tables of 90%, 95%, and 99% confidence limits, and comments on use" Am. J. Hum Genet 1988; 42:217-226.

Krex D., et al., "Identification of uncommon chromosomal aberrations in the neuroglioma cell line H4 by spectral karyotyping" J. Neurooncol. Apr. 2001: 52(2): 119-28.

Rummukainen J., et al., "Aberrations on chromosome 8 in 16 breast cancer cell lines by comparative genomic hybridization, fluorescence in situ hybridization, and spectral karyotyping" Cancer Genet Cytogenet Apr. 1, 2001; 126(1): 1-7.

* cited by examiner

*Primary Examiner*—Suryaprabha Chunduru
(74) *Attorney, Agent, or Firm*—Lowrie, Lando & Anastasi, LLP

(57) ABSTRACT

Disclosed are methods for identifying genetic mosaicisms in cell populations. Suitable cell populations include, e.g., biopsy or body fluid samples or cultures of cancer cells. The method includes performing array-based comparative genomic hybridization (CGH), wherein a plurality of cloned genomic nucleic acid segments is provided in a plurality of identical replicas, each cloned segment immobilized to a discrete and known spot on a substrate surface to form the array, and the cloned genomic nucleic acid segments comprise a substantially complete first genome of a known first karyotype. The invention also provides methods for optimizing performance of an array-based comparative genomic hybridization (CGH).

40 Claims, No Drawings

METHODS FOR DETECTING GENETIC MOSAICISMS USING ARRAYS

This application claims the benefit of U.S. Provisional patent application 60/325,853 dated Sep. 27, 2001.

TECHNICAL FIELD

This invention relates to molecular biology, genetic diagnostics and array, or "biochip," technology. In particular, the invention provides methods for determining genetic mosaicisms in cell populations, such as biopsy samples or cultures of cancer cells. The invention also provides methods for optimizing performance of an array-based comparative genomic hybridization (CGH).

BACKGROUND

Genomic DNA microarray based comparative genomic hybridization (CGH) has the potential to solve many of the limitations of traditional CGH method, which relies on comparative hybridization on individual metaphase chromosomes. In metaphase CGH, multi-megabase fragments of different samples of genomic DNA (e.g., known normal versus test, e.g., a possible tumor) are labeled and hybridized to a fixed chromosome (see, e.g., Breen (1999) J. Med. Genetics 36:511-517; Rice (2000) Pediatric Hematol. Oncol. 17:141-147). Signal differences between known and test samples are detected and measured. In this way, missing, amplified, or unique sequences in the test sample, as compared to "normal," can be detected by the fluorescence ratio of normal control to test genomic DNA. In metaphase CGH, the target sites (on the fixed chromosome) are saturated by an excess amount of soluble, labeled genomic DNA.

In contrast to metaphase CGH, where the immobilized genomic DNA is a metaphase spread, array-based CGH uses immobilized nucleic acids arranged as an array on a biochip or a microarray platform. The so-called array or chip CGH approach can provide DNA sequence copy number information across the entire genome in a single, timely, cost-effective and sensitive procedure, the resolution of which is primarily dependent upon the number, size and map positions of the DNA elements within the array. Typically, bacterial artificial chromosomes, or BACs, which can each accommodate on average about 150 kilobases (kb) of cloned genomic DNA, are used in the production of the array.

The principle of the array CGH approach is simple. Equitable amounts of total genomic DNA from cells of a test sample and a reference sample (e.g., a sample from cells known to be free of chromosomal aberrations) are differentially labeled with fluorescent dyes and co-hybridized to the array of BACs, which contain the cloned genomic DNA fragments that collectively cover the cell's genome. The resulting co-hybridization produces a fluorescently labeled array, the coloration of which reflects the competitive hybridization of sequences in the test and reference genomic DNAs to the homologous sequences within the arrayed BACs. Theoretically, the copy number ratio of homologous sequences in the test and reference genomic DNA samples should be directly proportional to the ratio of their respective fluorescent signal intensities at discrete BACs within the array. The versatility of the approach allows the detection of both constitutional variations in DNA copy number in clinical cytogenetic samples such as amniotic samples, chorionic villus samples (CVS), blood samples and tissue biopsies as well as somatically acquired changes in tumorigenically altered cells, for example, from bone marrow, blood or solid tumor samples.

While microarray genome profiling represents a revolutionary progression in genetic testing, certain limitations do persist. This is particularly true in the ability of microarray genome profiling to detect genetic mosaicism. Genetic mosaicism can be defined as the presence of two or more chromosomally distinct cell lines or cell lineages within a sample or a reference population of cells. For example, a solid tumor's ("a sample") genetic make-up can be 50% 47,XXX and 50% 45X,-X cells. Accurate measurement of the presence or degree of genetic mosaicism in a cell population can be helpful in determining the causality of a pathology (e.g., cancer) or a condition (e.g., an inherited chromosomal defect), or, to develop a more accurate diagnosis or prognosis of the pathology or condition.

Genetic mosaicism is routinely detected by conventional G-banding chromosome analysis, where the chromosomes of individual cells are analyzed. However, unlike the conventional cytogenetic approach of karyotype analysis, it is not the chromosomes of individual cells from a sample that are analyzed in microarray genome profiling, but rather the DNA sequence copy number of the total genomic DNA extracted from the cells of the sample. Consequently, from a DNA copy number perspective, the genome profile of the above tumor is no different from total genomic DNA extracted from a reference population of 46,XX cells. Hence, the genetic mosaicism of this tumor sample would not be detected by microarray genome profiling.

The above example, though hypothetical, illustrates the potential limitation of microarray genome profiling in the detection of genetic mosaicism. Nevertheless, in practice, the genetic mosaicisms observed in clinical samples will likely only rarely involve cell populations whose combined genetic profiles completely mask the presence of a mosaic population. Instead, the challenge to microarray genome profiling will come from the sensitivity with which it can detect clonally distinct cell populations within a more dominant background cell population. Conventional microarray genome profiling would not detect the genetic mosaicism in total genomic DNA from a patient whose constitutional genetic make-up was complex, for example, 47,XY,+21[7]/46,XY[13].

The degree of possible mosaicism can be correlated to the source of the clinical sample. For example, the degree and complexity of mosaicism observed in prenatal and non-cancer samples, in general, is rarely as striking as that observed in many tumorigenically altered cells. Mosaicism as it applies to non-cancer samples, in general, results from the inaccurate segregation of chromosomes at a post-fertilization, mitotic division. The degree of mosaicism is dependent on the stage of development at which the aberrant mitotic division occurred. For example, if the aberrant mitotic division was associated with the division of the zygote, then the level of mosaicism, or the percentage of cells harboring the chromosomally distinct constitution, may be as high as 50% in most if not all tissues. Alternatively, if the aberrant segregation occurred after the three primary cell types, ectoderm, mesoderm and endoderm have developed, the presence of abnormal cells may be confined solely to tissues derived from one of the primary cell types or even to a single organ of the body. Hence, from a genome profiling perspective, the detection of mosaicism in non-cancer samples is dependent upon two primary factors, namely, was the genomic DNA extracted from tissue harboring mosaic cells and secondly and what is the level of mosaicism within the tissue sample.

In contrast to the mosaicism observed in non-cancer samples, the mosaicism observed in many solid tumors and other tumorigenically altered cell populations usually results from a progressive clonal differentiation of cells. The resulting mosaicism can usually be far more complex than that observed in non-cancer samples. An actual example may serve to clarify the issue. Consider the following karyotype obtained by conventional G-banding analysis of a neoplastic population of cells:

46,XX,del(5)(q13)[7]/47,XX,del(5)(q13),+8[9]/48,XX, del(5) (q13),+8,+9 [9].

The following can be inferred from this karyotype: Chromosome analyses were performed on a total of 25 cells from this neoplastic cell population (the summation of the numbers in the [] brackets, i.e. 7+9+9). From this analysis it can be determined that the deletion of the q13 band on chromosome 5 was associated with an initial neoplastic event. However, it appears that as this neoplastic event continued, a second clone developed with a gain of chromosome 8 (as designed by the "+8"), and then another from this latter clone with a gain of chromosome 9 (as designed by the "+8,+9"). Therefore, while 100% of the total genomic DNA extracted from these cells will contain the deletion of 5q13, 72% ((9+9)/25) will be trisomic for chromosome 8 and only 36% (9/25) will be trisomic for chromosome 9. Hence, from a quality control perspective, in this example, the challenge to microarray genome profiling would be whether or not it could detect the trisomic event if it only occurred in 36% of the total genomic DNA or even 72% of the DNA.

SUMMARY

The invention provides a method of detecting a genetic mosaicism in a cell population by performing an array-based comparative genomic hybridization (CGH), comprising the following steps: (a) providing an array comprising a plurality of cloned genomic nucleic acid segments, wherein each genomic nucleic acid segment is immobilized to a discrete and known spot on a substrate surface to form an array and the cloned genomic nucleic acid segments comprise a substantially complete first genome of a known karyotype; (b) providing a first sample, wherein the sample comprises a plurality of genomic nucleic acid segments comprising a substantially complete complement of the first genome labeled with a first detectable label; (c) providing a second sample, wherein the sample comprises a plurality of genomic nucleic acid labeled with a second detectable label, and the genomic nucleic acid sample comprises a substantially complete complement of genomic nucleic acid of a cell or a tissue sample, and the karyotype of the second sample is known and is different from that of the first sample of step (b); (d) providing a third sample, wherein the sample comprises a genomic nucleic acid sample with an unknown karyotype labeled with the second detectable label, and the genomic nucleic acid comprises a substantially complete complement of genomic nucleic acid of a cell or a tissue sample; (e) preparing serial dilution fractions of the samples of steps (c) and (d); (f) contacting the sample of step (b) separately with each serial dilution fraction of the sample of step (c) with the array of step (a) under conditions wherein the nucleic acid in the samples can specifically hybridize to the genomic nucleic acid segments immobilized on the array; (g) measuring the amount of first and second fluorescent label on each spot after the contacting of step (f) for each serial dilution fraction and determining the karyotype of each serial dilution fraction by comparative genomic hybridization; (h) contacting the sample of step (b) and serial dilution fractions of the sample of step (d) with the array of step (a) under conditions wherein the nucleic acid in the samples can specifically hybridize to the genomic nucleic acid segments on the array; (i) measuring the amount of first and second fluorescent label on each spot after the contacting of step (h) for each serial dilution fraction and determining the karyotype of each serial dilution fraction by comparative genomic hybridization; and, (j) selecting which dilution fraction karyotype determination of step (g) most closely determined the known karyotype, and selecting the same serial dilution measurement in step (i) to determine the karyotype of the sample of step (d), thereby determining the degree of genetic mosaicism in a cell population.

The cell population can comprise any cell type, e.g., mammalian cells, such as human cells. In one aspect, the cell population is derived from an individual suspected of having a chromosomal abnormality. In one aspect, the cell population is derived from an individual suspected of having a disease or condition associated with a karyotype abnormality. The disease or condition can comprise any kind of cancer, including benign or neoplastic tumors or hyperplastic growths.

In one aspect, the cell population is from a body fluid sample or a tissue sample. The body fluid or tissue sample can comprise a cancer cell, a tumor cell or a hyperplastic tissue cell sample. The cell population can be from a biopsy sample, a blood sample, a chorionic villus sample, an embryonic cell or embryo tissue sample, a chord blood sample, and the like.

In one aspect, the substantially complete genome comprises a mammalian genome, such as a human genome. In one aspect, the array-immobilized genome, the first genome, the second genome and the genome of unknown karyotype are derived from the same species. The species can be a mammal, such as a human.

In one aspect, a cloned nucleic acid segment used in the methods is cloned in a construct comprising an artificial chromosome, such as a bacterial artificial chromosome (BAC), a human artificial chromosome (HAC), a yeast artificial chromosome (YAC), a transformation-competent artificial chromosome (TAC) and a bacteriophage P1-derived artificial chromosome (PAC). A cloned nucleic acid segment can be cloned in a construct comprising a vector selected from the group consisting of a cosmid vector, a plasmid vector and a viral vector.

In one aspect, the cloned nucleic acid segment is between about 50 kilobases (0.5 megabase) to about 500 kilobases (5 megabases) in length. The cloned nucleic acid segment can be between about 100 kilobases (1 megabase) to about 400 kilobases (4 megabases) in length. The cloned nucleic acid segment can be about 300 kilobases (3 megabases) in length.

In one aspect, the karyotype of the first genome is determined by conventional G-banding analysis, FISH or SKY or a combination thereof. Thus, in one aspect, karyotype of the array-immobilized genome is known.

In one aspect, the detectable label comprises a fluorescent label, such as a Cy5™ or equivalent, a Cy3™ or equivalent, a rhodamine, a fluorescein or an aryl-substituted 4,4-difluoro-4-bora-3a, 4a-diaza-s-indacene dye or equivalents.

In alternative aspects, labeling of the genomic nucleic acid segments comprises random prime labeling, nick translation labeling, amplification label incorporation or a combination thereof.

In one aspect, the array-immobilized genome comprises a wild type karyotype, i.e., a wild type genome (which sometimes is referred to as a "normal genome" or "normal karyotype"). The first sample can also comprise a wild type karyotype (wild type, or normal, genome).

In one aspect, the second sample comprises a cancer cell population, which can be a population comprising a mosaic karyotype. The second sample can comprise a mosaic karyotype comprising two or more cell subpopulations, wherein each subpopulation comprises a different karyotype.

In one aspect, the array-immobilized genomic nucleic acid segments in a first spot are non-overlapping in sequence compared to the array-immobilized genomic nucleic acid segments in a second spot. The array-immobilized genomic nucleic acid segments in a spot can be non-overlapping in sequence compared to the array-immobilized genomic nucleic acid segments all of other genomic nucleic acid-comprising spots on the array. In one aspect, each cloned genomic nucleic acid segment is spotted in duplicate on the array.

In one aspect, about 75%, 80%, 85%, 90%, 95%, 98%, 99%, or 100% of the array-immobilized genomic nucleic acid comprise a detectable label. The array-immobilized genomic nucleic acid can comprise a third detectable label.

In one aspect, the array-immobilized genomic nucleic acid are covalently bound to the substrate surface. The array-immobilized genomic nucleic acid can be covalently bound to a compound having the general formula: R1—X—R2, wherein R1 is a cyclic ether, an aldehyde, or a chloromethylphenyl moiety; X is a moiety chemically suitable for linking the R1 moiety to the R2 moiety, and the R2 moiety has the general formula

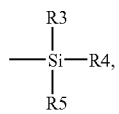

wherein R3, R4 and R5 comprise identical or different alkoxy group or chloro groups.

In one aspect, the array-immobilized genomic nucleic acid are covalently bound to a compound having the general formula: R1—X—R2, wherein R1 is an amino group, R2 is an alkoxysilane group or a chlorohalide group; and X is a moiety chemically suitable for linking the R1 group and the R2 group. The array-immobilized genomic nucleic acid can be covalently bound to a compound having the general formula

wherein m+k is the integer 3, and n can be 0 if m is greater than 0, or n+k is the integer 3 and m can be 0 if n is greater than 0; X is an inert linker; R1 comprises a group reactive toward the biological molecule; R is an alkyl group; and, R2 is an alkyl group.

In one aspect, the array comprises a SpectralChip™ Mouse BAC Array, or a SpectralChip™ Human BAC Array.

In alternative aspect, the serial dilutions are two-fold dilutions, three-fold, four-fold, five-fold, six-fold, seven fold, eight-fold, nine-fold or ten-fold dilutions.

The methods can further comprise use of a device that can measure which detectable labels are on which spots on the substrate surface. The device can comprise a charge-coupled device (CCD). The device can be capable of multicolor fluorescence imaging. The methods can further comprise use of a computer processor and/or computer implemented analytical methods to analyze multicolor fluorescence imaging data. The methods can further comprise use of a computer and a computer program algorithms to interpret data imaged from the array and display results of a karyotype analysis.

The invention comprises a method of detecting the degree of genetic mosaicism in a cancer cell population by performing an array-based comparative genomic hybridization (CGH), comprising the following steps: (a) providing an array comprising a plurality of cloned genomic nucleic acid segments, wherein each genomic nucleic acid segment is immobilized to a discrete and known spot on a substrate surface to form an array and the cloned genomic nucleic acid segments comprise a substantially complete first genome of a known karyotype; (b) providing a first sample, wherein the sample comprises a plurality of genomic nucleic acid segments comprising a substantially complete complement of the first genome labeled with a first detectable label; (c) providing a second sample, wherein the sample comprises a plurality of genomic nucleic acid labeled with a second detectable label, and the genomic nucleic acid sample comprises a substantially complete complement of genomic nucleic acid of a cell or a tissue sample, and the karyotype of the second sample is known and is different from that of the first sample of step (b); (d) providing a third sample, wherein the sample comprises a genomic nucleic acid sample with an unknown karyotype labeled with the second detectable label, and the genomic nucleic acid comprises a substantially complete complement of genomic nucleic acid of a cancer or a tumor; (e) preparing serial dilution fractions of the samples of steps (c) and (d); (f) contacting the sample of step (b) separately with each serial dilution fraction of the sample of step (c) with the array of step. (a) under conditions wherein the nucleic acid in the samples can specifically hybridize to the genomic nucleic acid segments immobilized on the array; (g) measuring the amount of first and second fluorescent label on each spot after the contacting of step (f) for each serial dilution fraction and determining the karyotype of each serial dilution fraction by comparative genomic hybridization; (h) contacting the sample of step (b) and serial dilution fractions of the sample of step (d) with the array of step (a) under conditions wherein the nucleic acid in the samples can specifically hybridize to the genomic nucleic acid segments on the array; (i) measuring the amount of first and second fluorescent label on each spot after the contacting of step (h) for each serial dilution fraction and determining the karyotype of each serial dilution fraction by comparative genomic hybridization; and, (j) selecting which dilution fraction karyotype determination of step (g) most closely determined the known karyotype, and selecting the same serial dilution measurement in step (i) to determine the karyotype of the sample of step (d), thereby determining the degree of genetic mosaicism in the cancer cell population. In alternative aspects, the cancer cell population comprises a sample from a tumor, including benign or neoplastic tumors, and, hyperplastic cell growths.

The invention provides a method of detecting a genetic mosaicism in a cell population by performing an array-based comparative genomic hybridization (CGH), comprising the following steps: (a) providing an array comprising a plurality of cloned genomic nucleic acid segments, wherein each genomic nucleic acid segment is immobilized to a discrete and known spot on a substrate surface to form an array and the cloned genomic nucleic acid segments comprise a substantially complete first genome of a known karyotype; (b) providing a first sample, wherein the sample comprises a plurality of genomic nucleic acid segments comprising a substantially complete complement of the first genome labeled with a first detectable label; (c) providing a second sample, wherein the sample comprises a plurality of genomic nucleic acid labeled with a second detectable label, and the genomic nucleic acid sample comprises a substantially complete complement of genomic nucleic acid of a cell or a tissue sample, and the karyotype of the second sample is known and is different from that of the first sample of step (b); (d) providing a third sample, wherein the sample comprises a genomic nucleic acid sample with an unknown karyotype labeled with the second detectable label, and the genomic nucleic acid comprises a substantially complete complement of genomic nucleic acid of a cell or a tissue sample; (e) preparing multiple fractions of the samples of steps (c) and (d); (f) contacting the sample of step (b) separately with the fractions of the sample of step (c) with the array of step (a) under varying conditions; (g) measuring the amount of first and second fluorescent label on each spot after the contacting of step (f) for each fraction and determining the karyotype of each fraction by comparative genomic hybridization; (h) contacting the sample of step (b) and serial dilution fractions of the sample of step (d) with the array of step (a) under varying conditions; (i) measuring the amount of first and second fluorescent label on each spot after the contacting of step (h) for each fraction and determining the karyotype of each fraction by comparative genomic hybridization; and, (j) selecting which fraction karyotype determination of step (g) most closely determined the known karyotype, and selecting the same conditions in step (i) to determine the karyotype of the sample of step (d), thereby determining the degree of genetic mosaicism in a cell population.

In alternative aspects, varying the conditions comprises varying temperature used in hybridization conditions or wash conditions for each fraction. Varying the conditions can comprise varying osmolarity of a hybridization buffer or a wash buffer used for each fraction. Varying the osmolarity can comprise varying the salt concentration of a hybridization buffer or a wash buffer used for each fraction. Varying the conditions can comprise varying the time each fraction is contacted to be array before reading the amount of sample bound to the array or before washing. Varying the conditions can comprise varying the time each fraction is washed after the contacting step and before reading the amount of sample bound to the array. Varying the conditions can comprise varying the concentration of nucleic acid used in each fraction. Varying the conditions can comprise varying the size of the nucleic acid used in each fraction. Varying the osmolarity can comprise varying the salt concentration of a hybridization buffer or a wash buffer used for each fraction. Varying the conditions can comprise varying the humidity of the hybridization conditions or the washing conditions.

The invention provides a method of detecting a genetic mosaicism in a human cell population by performing an array-based comparative genomic hybridization (CGH), comprising the following steps: (a) providing an array comprising a plurality of cloned human genomic nucleic acid segments, wherein each genomic nucleic acid segment is immobilized to a discrete and known spot on a substrate surface to form an array and the cloned genomic nucleic acid segments comprise a substantially complete first human genome of a normal karyotype; (b) providing a first sample, wherein the sample comprises a plurality of genomic human nucleic acid segments comprising a substantially complete complement of the first human genome labeled with a first detectable label; (c) providing a second sample, wherein the sample comprises a plurality of human genomic nucleic acid labeled with a second detectable label, and the genomic nucleic acid sample comprises a substantially complete complement of genomic nucleic acid of a cell or a tissue sample, and the karyotype of the second sample is known and is different from that of the first sample of step (b); (d) providing a third sample, wherein the sample comprises a second detectable genomic human nucleic acid sample with an unknown karyotype labeled with the second detectable label, and the genomic nucleic acid comprises a substantially complete complement of genomic nucleic acid of a cell or a tissue sample; (e) preparing serial dilution fractions of the samples of steps (c) and (d); (f) contacting the sample of step (b) separately with each serial dilution fraction of the sample of step (c) with the array of step (a) under conditions wherein the nucleic acid in the samples can specifically hybridize to the genomic nucleic acid segments immobilized on the array; (g) measuring the amount of first and second fluorescent label on each spot after the contacting of step (f) for each serial dilution fraction and determining the karyotype of each serial dilution fraction by comparative genomic hybridization; (h) contacting the sample of step (b) and serial dilution fractions of the sample of step (d) with the array of step (a) under conditions wherein the nucleic acid in the samples can specifically hybridize to the genomic nucleic acid segments on the array; (i) measuring the amount of first and second fluorescent label on each spot after the contacting of step (h) for each serial dilution fraction and determining the karyotype of each serial dilution fraction by comparative genomic hybridization; and, (j) selecting which dilution fraction karyotype determination of step (g) most closely determined the known karyotype, and selecting the same serial dilution measurement in step (i) to determine the karyotype of the sample of step (d), thereby determining the degree of genetic mosaicism in a cell population.

The invention provides a method of optimizing performance of an array-based comparative genomic hybridization (CGH), comprising the following steps: (a) providing an array comprising a plurality of cloned genomic nucleic acid segments, wherein each genomic nucleic acid segment is immobilized to a discrete and known spot on a substrate surface to form an array and the cloned genomic nucleic acid segments comprise a substantially complete first genome of a known karyotype; (b) providing a first sample, wherein the sample comprises a plurality of genomic nucleic acid segments comprising a substantially complete complement of the first genome labeled with a first detectable label; (c) providing a second sample, wherein the sample comprises a plurality of genomic nucleic acid labeled with a second detectable label, and the genomic nucleic acid sample comprises a substantially complete complement of genomic nucleic acid of a cell or a tissue sample, and the karyotype of the second sample is known and is different from that of the first sample of step (b); (d) preparing serial dilution fractions of the samples of step (c); (e) contacting the sample of step (b) separately with each serial dilution fraction of the sample of step (c) with the array of step (a) under conditions wherein the nucleic acid in the samples can specifically hybridize to the genomic nucleic acid segments immobilized on the array; (f) measuring the amount of first and second fluorescent label on each spot after the contacting of step (e) for each serial dilution fraction and determining the karyotype of each serial dilution fraction by comparative genomic hybridization; (h) selecting which dilution fraction karyotype determination of step (f) most closely determined the known karyotype of the genome of step (a) and step (b), and using that dilution for karyotype determinations of unknown samples comprising genomic DNA of a similar specie on the array used in step (a). In one aspect, the species is a mammal, such as a human.

The invention provides a method of optimizing performance of an array-based comparative genomic hybridization (CGH), comprising the following steps: (a) providing an array comprising a plurality of cloned genomic nucleic acid segments, wherein each genomic nucleic acid segment is immobilized to a discrete and known spot on a substrate surface to form an array and the cloned genomic nucleic acid segments comprise a substantially complete first genome of a known karyotype; (b) providing a first sample, wherein the sample comprises a plurality of genomic nucleic acid segments comprising a substantially complete complement of the first genome labeled with a first detectable label; (c) providing a second sample, wherein the sample comprises a plurality of genomic nucleic acid labeled with a second detectable label, and the genomic nucleic acid sample comprises a substantially complete complement of genomic nucleic acid of a cell or a tissue sample, and the karyotype of the second sample is known and is different from that of the first sample of step (b); (d) preparing fractions of the samples of step (c); (e) contacting the sample of step (b) separately with the fractions of the sample of step (c) with the array of step (a) under varying conditions; (f) measuring the amount of first and second fluorescent label on each spot after the contacting of step (e) for each dilution fraction and determining the karyotype of each dilution fraction by comparative genomic hybridization; (g) selecting which fraction karyotype determination of step (f) most closely determined the known karyotype of the genome of step (a) and step (b), and using that condition for karyotype determinations of unknown samples comprising genomic DNA of a similar specie on the array used in step (a). In one aspect, the fractions comprise equal amounts of nucleic acid.

In alternative aspects, varying the conditions comprises varying temperature used in hybridization conditions or wash conditions for each fraction. Varying the conditions can comprise varying osmolarity of a hybridization buffer or a wash buffer used for each fraction. Varying the osmolarity can comprise varying the salt concentration of a hybridization buffer or a wash buffer used for each fraction. Varying the conditions can comprise varying the time each fraction is contacted to be array before reading the amount of sample bound to the array or before washing. Varying the conditions can comprise varying the time each fraction is washed after the contacting step and before reading the amount of sample bound to the array. Varying the conditions can comprise varying the concentration of nucleic acid used in each fraction. Varying the conditions can comprise varying the size of the nucleic acid used in each fraction. Varying the osmolarity can comprise varying the salt concentration of a hybridization buffer or a wash buffer used for each fraction. Varying the conditions can comprise varying the humidity of the hybridization conditions or the washing conditions.

The details of one or more embodiments of the invention are set forth in the accompanying drawings and the description below. Other features, objects, and advantages of the invention will be apparent from the description and drawings, and from the claims.

All publications, patents, patent applications, GenBank sequences and ATCC deposits cited herein are hereby expressly incorporated by reference for all purposes.

DETAILED DESCRIPTION

The invention provides novel array-based methods for determining levels of mosaicism in a sample, such as a cell, a tissue or a cell culture population. The methods of the invention provide to microarray genome profiling the sensitivity to detect clonally distinct cell subpopulations. The methods of the invention are sufficiently sensitive to detect clonally distinct (by karyotypic criteria) cell populations within a more dominant background cell population. Thus, the methods of the invention are particularly suited for accurate determination and analysis of the complex level of genetic mosaicism frequently observed in many solid tumors and other tumorigenically altered cells and samples from individuals with a complex, aberrant genetic make-up.

In one aspect, the methods of the invention determine the sensitivity of a microarray in detecting a genetic mosaicism. Total genomic DNA is isolated from a cell population, e.g., a cancer cell population, with a predetermined level of mosaicism. The level of genetic mosaicism can be predetermined by any means, e.g., by conventional G-band karyotyping, also referred to as "GTG-banding technique" (see, e.g., Scheres (1982) Hum. Genet. 61:8-11; Wakui (1999) J. Hum. Genet. 44:85-90); by fluorescence in situ hybridization ("FISH") (see, e.g., Zhao (2000) Cancer Genet. Cytogenet. 118:108-111); or by spectral karyotyping ("SKY") (see, e.g., Veldman (1997) Nat. Genet. 15:406-410) or a combination thereof (see, e.g., Zhao (2001) Cancer Genet. Cytogenet. 127:143-147). The microarray genome profile of the total genomic DNA from this cell population is performed and the number of clonal subpopulations with distinct karyotypes and their respective percentages in the total population are measured. These array-based results are then compared to the results of a karyotype analysis by conventional, non-array methodologies (e.g., G-band karyotyping, FISH, SKY). The degree of consistency of the karyotype analyses between the conventional method(s) and the array-based method are compared and catalogued.

In another aspect, pre-isolated total genomic DNA from a homogenous population of cells with a known chromosomal aberration (as predetermined by conventional means, as discussed above) are used in a set of serial dilutions with isolated genomic DNA from "normal cells" with a "normal karyotype," e.g., cells with no known chromosomal aberrations. For example, the microarray genome profile on total genomic DNA has been established for a female abortus with a deletion of Xq and simultaneous trisomy of 16q. Serial dilutions of this test genomic DNA with normal 46,XX genomic DNA are performed. Each dilution DNA mix is analyzed by microarray genome profiling. The karyotypic analysis results of each dilution are compared to the results acquired by conventional means. The serial dilution giving the most accurate karyotype profile is determined, providing a guideline for serially diluting an unknown test, e.g., clinical, sample, such as a biopsy or culture of cancer cells. Thus, the methods of the invention increase the sensitivity of detection of mosaic populations by an array.

By providing a means to determine the capacity of an array to detect complex subsets of differing genomes in a sample, i.e., genetic mosaicism, using the methods of the invention, the presence and degree of genetic heterogeneity in a cell population can be accurately determined. Use of the methods of the invention allows accurate microarray genome profiling to detect the genetic mosaicism in total genomic DNA from a patient or a sample whose constitutional genetic make-up is complex, for example, 47,XY,+21[7]/46,XY[13], or, 46,XX,del(5)(q13)[7]/47, XX,del(5)(q13),+8[9]/ 48,XX,del(5)(q13),+8[9], as discussed in the background section, above.

As another example, with the methods of the invention, using microarrays it is possible to ascertain that the total genomic DNA extracted from a neoplastic cell sample (the sample of "unknown karyotype"), which has a complex karyotype equivalent to 46,XX,del(5)(q13)[7]/47,XX,del(5)(q13),+8[9]/48,XX,del(5)(q13), +8,+9[9], contains the deletion of 5q13, 72% ((9+9)/25) being trisomic for chromosome 8 and only 36% (9/25) being trisomic for chromosome 9. Hence, from a quality control perspective, in this example, with the methods of the invention the microarray genome profiling could detect the trisomic event if it only occurred in 36% of the total genomic DNA. Microarray genome profiling with the methods of the invention can detect subpopulations that are less than 36% of the total genomic DNA.

In one aspect, a contiguous series of artificial mosaic populations for both chromosomal gains and losses can be determined. Furthermore, use of the methods of the invention precludes the need to computate confidence parameters, e.g., to rule out the presence of mosaicism within a given confidence level as described by Hook (1988) Am. J. Hum. Genet. 42: 217-226; Claussen (1984) Hum. Genet. 67:23-28; or, Cheung (1990) Prenat. Diagn. 10:41-57, as needed when using conventional G-banding chromosome analyses.

DEFINITIONS

Unless defined otherwise, all technical and scientific terms used herein have the meaning commonly understood by a person skilled in the art to which this invention belongs. As used herein, the following terms have the meanings ascribed to them unless specified otherwise.

The terms "array" or "microarray" or "DNA array" or "nucleic acid array" or "chip" or "biochip" as used herein is a plurality of target elements, each target element comprising a defined amount of one or more biological molecules, e.g., nucleic acids, immobilized on a defined location on a substrate surface; as described in further detail, below.

The term "aryl-substituted 4,4-difluoro-4-bora-3a, 4a-diaza-s-indacene dye" as used herein includes all "boron dipyrromethene difluoride fluorophore" or "BODIPY" dyes and "dipyrromethenboron difluoride dyes" (see, e.g., U.S. Pat. No. 4,774,339), or equivalents, are a class of fluorescent dyes commonly used to label nucleic acids for their detection when used in hybridization reactions; see, e.g., Chen (2000) J. Org Chem. 65:2900-2906: Chen (2000) J. Biochem. Biophys. Methods 42:137-151. See also U.S. Pat. Nos. 6,060,324; 5,994,063; 5,614,386; 5,248,782; 5,227,487; 5,187,288.

The terms "cyanine 5" or "Cy5™" and "cyanine 3" or "Cy3™" refer to fluorescent cyanine dyes produced by Amersham Pharmacia Biotech (Piscataway, N.J.) (Amersham Life Sciences, Arlington Heights, Ill.), as described in detail, below, or equivalents. See U.S. Pat. Nos. 6,027,709; 5,714,386; 5,268,486; 5,151,507; 5,047,519. These dyes are typically incorporated into nucleic acids in the form of 5-amino-propargyl-2'-deoxycytidine 5'-triphosphate coupled to Cy5™ or Cy3™.

The terms "fluorescent dye" and "fluorescent label" as used herein includes all known fluors, including rhodamine dyes (e.g., tetramethylrhodamine, dibenzorhodamine, see, e.g., U.S. Pat. No. 6,051,719); fluorescein dyes; "BODIPY" dyes and equivalents (e.g., dipyrromethenboron difluoride dyes, see, e.g., U.S. Pat. No. 5,274,113); derivatives of 1-[isoindolyl]methylene-isoindole (see, e.g., U.S. Pat. No. 5,433,896); and all equivalents. See also U.S. Pat. Nos. 6,028,190; 5,188,934.

The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions. The term "stringent conditions" refers to conditions under which one nucleic acid will hybridize preferentially to second sequence (e.g., a sample genomic nucleic acid hybridizing to an immobilized nucleic acid probe in an array), and to a lesser extent to, or not at all to, other sequences. A "stringent hybridization" and "stringent hybridization wash conditions" in the context of nucleic acid hybridization (e.g., as in array, Southern or Northern hybridizations) are sequence dependent, and are different under different environmental parameters. Stringent hybridization conditions as used herein can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Those of ordinary skill will readily recognize that alternative but comparable hybridization and wash conditions can be utilized to provide conditions of similar stringency.

However, the selection of a hybridization format is not critical, as is known in the art, it is the stringency of the wash conditions that set forth the conditions which determine whether a soluble, sample nucleic acid will specifically hybridize to an immobilized nucleic acid. Wash conditions can include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be, e.g., 0.2×SSC/0.1% SDS at 42° C. See Sambrook, Ausubel, or Tijssen (cited herein) for detailed descriptions of equivalent hybridization and wash conditions and for reagents and buffers, e.g., SSC buffers and equivalent reagents and conditions.

The term "karyotype" means the genetic makeup, or chromosome composition, of a cell or cell population. The term "karyotype" has also been used to mean the complete chromosome set of the nucleus of a cell, and the chromosomal complement of an individual or sample, including the number of chromosomes and any abnormalities. The methods of the invention are used to determine the karyotype of a cell population, which includes an determination of the genetic mosaicism of a cell population, including the number of karyotype subpopulations in a sample and the percent of the cell population having a particular karyotype.

Because specific diseases and conditions have characteristic karyotypes, characterization of the karyotype of a cell or cell population can be used to diagnose, detect or prognose those diseases and conditions. Similarly, because levels of genetic mosaicisms in a cancer or tumor population can be indicative of its behavior and physiology, e.g., its tumorigenicity, determination of the genetic mosaicism of a cancer is useful for diagnosis, prognosis and treatment planning.

The phrase "labeled with a detectable composition" or "labeled with a detectable moiety" as used herein refers to a nucleic acid comprising a detectable composition, i.e., a label, as described in detail, below. The label can also be another biological molecule, as a nucleic acid, e.g., a nucleic acid in the form of a stem-loop structure as a "molecular beacon," as described below. This includes incorporation of labeled bases (or, bases which can bind to a detectable label) into the nucleic acid by, e.g., nick translation, random primer extension, amplification with degenerate primers, and the like. The label can be detectable by any means, e.g., visual, spectroscopic, photochemical, biochemical, immunochemical, physical or chemical means. Examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin.

The term "nucleic acid" as used herein refers to a deoxyribonucleotide or ribonucleotide in either single- or double-stranded form. The term encompasses nucleic acids containing known analogues of natural nucleotides. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923-1937; Antisense Research and Applications (1993, CRC Press). PNAs contain non-ionic backbones, such as N-(2-aminoethyl) glycine units. Phosphorothioate linkages are described, e.g., by U.S. Pat. Nos. 6,031,092; 6,001,982; 5,684,148; see also, WO 97/03211; WO 96/39154; Mata (1997) Toxicol. Appl. Pharmacol. 144:189-197. Other synthetic backbones encompassed by the term include methyl-phosphonate linkages or alternating methylphosphonate and phosphodiester linkages (see, e.g., U.S. Pat. No. 5,962,674; Strauss-Soukup (1997) Biochemistry 36:8692-8698), and benzylphosphonate linkages (see, e.g., U.S. Pat. No. 5,532,226; Samstag (1996) Antisense Nucleic Acid Drug Dev 6:153-156). The term nucleic acid is used interchangeably with gene, DNA, RNA, cDNA, mRNA, oligonucleotide primer, probe and amplification product.

The term "genomic DNA" or "genomic nucleic acid" includes nucleic acid isolated from a nucleus of one or more cells, and, includes nucleic acid derived from (e.g., isolated from, amplified from, cloned from, synthetic versions of) genomic DNA. The genomic DNA can be from any source, as discussed in detail, below.

The term "a sample comprising a nucleic acid" or "sample of nucleic acid" as used herein refers to a sample comprising a DNA or an RNA, or nucleic acid representative of DNA or RNA isolated from a natural source, in a form suitable for hybridization (e.g., as a soluble aqueous solution) to another nucleic acid or polypeptide or combination thereof (e.g., immobilized probes). The nucleic acid may be isolated, cloned or amplified; it may be, e.g., genomic DNA, mRNA, or cDNA from substantially an entire genome, substantially all or part of a particular chromosome, or selected sequences (e.g. particular promoters, genes, amplification or restriction fragments, cDNA library, etc.). The nucleic acid sample may be extracted from particular cells, tissues or body fluids, or, can be from cell cultures, including cell lines, or from preserved tissue sample, as described in detail, below.

As used herein, the terms "computer" and "processor" are used in their broadest general contexts and incorporate all such devices. The methods of the invention can be practiced using any computer/processor and in conjunction with any known software or methodology. For example, a computer/processor can be a conventional general-purpose digital computer, e.g., a personal "workstation" computer, including conventional elements such as microprocessor and data transfer bus. The computer/processor can further include any form of memory elements, such as dynamic random access memory, flash memory or the like, or mass storage such as magnetic disc optional storage.

Generating and Manipulating Nucleic Acids

Practicing the methods of the invention may involve the isolation, synthesis, cloning, amplification, labeling and hybridization (e.g., CGH) of nucleic acids. As described herein, the nucleic acid for analysis and the immobilized nucleic acid on the array can be representative of genomic DNA, including defined parts of, or entire, chromosomes, or entire genomes. Comparative genomic hybridization (CGH) reactions, see, e.g., U.S. Pat. Nos. 5,830,645; 5,976,790, are discussed in further detail, below. Nucleic acid samples are labeled with a detectable moiety, e.g., a fluorescent dye. For example, a first sample can labeled with a fluor and a second sample labeled with a second dye (e.g., Cy3™ and Cy5™). In one aspect, the each sample nucleic acid is labeled with at least one different detectable moiety, e.g., different fluorescent dyes, than those used to label the other samples of nucleic acids.

In some cases, the nucleic acids may be amplified using standard techniques such as PCR. Amplification can also be used to subclone or label the nucleic acid prior to the hybridization. The sample and/or the immobilized nucleic acid can be labeled, as described herein. The sample or the probe on the array an be produced from and collectively can be representative of a source of nucleic acids from one or more particular (pre-selected) portions of, e.g., a collection of polymerase chain reaction (PCR) amplification products, substantially an entire chromosome or a chromosome fragment, or substantially an entire genome, e.g., as a collection of clones, e.g., BACs, PACs, YACs, and the like (see below). The array-immobilized nucleic acid or genomic nucleic acid sample may be processed in some manner, e.g., by blocking or removal of repetitive nucleic acids or by enrichment with selected nucleic acids.

Samples are applied to the immobilized probes (e.g., on the array) and, after hybridization and washing, the location (e.g., spots on the array) and amount of each dye are read. The immobilized nucleic acid can be representative of any part of or all of a chromosome or genome. The array-immobilized nucleic acid can be in the form of cloned DNA, e.g., YACs, BACs, PACs, and the like, as described herein. As is typical of array technology, in one aspect, each "spot" on the array has a known sequence, e.g., a known segment of genome or other sequence. The invention can be practiced in conjunction with any method or protocol or device known in the art, which are well described in the scientific and patent literature.

General Techniques

The nucleic acids used to practice this invention, whether RNA, cDNA, genomic DNA, vectors, viruses or hybrids thereof, may be isolated from a variety of sources, genetically engineered, amplified, and/or expressed/generated recombinantly. Any recombinant expression system can be used, including, in addition to bacterial cells, e.g., mammalian, yeast, insect or plant cell expression systems.

Alternatively, these nucleic acids can be synthesized in vitro by well-known chemical synthesis techniques, as described in, e.g., Carruthers (1982) Cold Spring Harbor Symp. Quant. Biol. 47:411-418; Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066. Double stranded DNA fragments may then be obtained either by synthesizing the complementary strand and annealing the strands together under appropriate conditions, or by adding the complementary strand using DNA polymerase with a primer sequence.

Techniques for the manipulation of nucleic acids, such as, e.g., subcloning, labeling probes (e.g., random-primer labeling using Klenow polymerase, nick translation, amplification), sequencing, hybridization, G-banding, SKY, FISH and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Cloning of Genomic Nucleic Acids

Genomic nucleic acids used in the methods of the invention, e.g., those immobilized onto arrays or used as samples, can be obtained and manipulated by cloning into various vehicles. If necessary, genomic nucleic acid samples can be screened and re-cloned or amplified from any source of genomic DNA. Thus, in various aspects, forms of genomic nucleic acid used in the methods of the invention (including arrays and samples) include genomic DNA, e.g., genomic libraries, contained in mammalian and human artificial chromosomes, satellite artificial chromosomes, yeast artificial chromosomes, bacterial artificial chromosomes, P1 artificial chromosomes, and the like.

Mammalian artificial chromosomes (MACs) and human artificial chromosomes (HAC) are, e.g., described in Ascenzioni (1997) Cancer Lett. 118:135-142; Kuroiwa (2000) Nat. Biotechnol. 18:1086-1090; U.S. Pat. Nos. 5,288,625; 5,721,118; 6,025,155; 6,077,697). MACs can contain inserts larger than 400 kilobase (Kb), see, e.g., Mejia (2001) Am. J. Hum. Genet. 69:315-326. Auriche (2001) EMBO Rep. 2:102-107, has built a human minichromosomes having a size of 5.5 kilobase.

Satellite artificial chromosomes, or, satellite DNA-based artificial chromosomes (SATACs), are, e.g., described in Warburton (1997) Nature 386:553-555; Roush (1997) Science 276:38-39; Rosenfeld (1997) Nat. Genet. 15:333-335). SATACs can be made by induced de novo chromosome formation in cells of different mammalian species; see, e.g., Hadlaczky (2001) Curr. Opin. Mol. Ther. 3:125-132; Csonka (2000) J. Cell Sci. 113 (Pt 18):3207-3216.

Yeast artificial chromosomes (YACs) can also be used and typically contain inserts ranging in size from 80 to 700 kb. YACs have been used for many years for the stable propagation of genomic fragments of up to one million base pairs in size; see, e.g., U.S. Pat. Nos. 5,776,745; 5,981,175; Feingold (1990) Proc. Natl. Acad. Sci. USA 87:8637-8641; Tucker (1997) Gene 199:25-30; Adam (1997) Plant J.11:1349-1358; Zeschnigk (1999) Nucleic Acids Res. 27:21.

Bacterial artificial chromosomes (BACs) are vectors that can contain 120, Kb or greater inserts, see, e.g., U.S. Pat. Nos. 5,874,259; 6,277,621; 6,183,957. BACs are based on the E. coli F factor plasmid system and simple to manipulate and purify in microgram quantities. Because BAC plasmids are kept at one to two copies per cell, the problems of rearrangement observed with YACs, which can also be employed in the present methods, are eliminated; see, e.g., Asakawa (1997) Gene 69-79; Cao (1999) Genome Res. 9:763-774.

P1 artificial chromosomes (PACs), bacteriophage P1-derived vectors are, e.g., described in Woon (1998) Genomics 50:306-316; Boren (1996) Genome Res. 6:1123-1130; Ioannou (1994) Nature Genet. 6:84-89; Reid (1997) Genomics 43:366-375; Nothwang (1997) Genomics 41:370-378; Kern (1997) Biotechniques 23:120-124). P1 is a bacteriophage that infects E. coli that can contain 75 to 100 Kb DNA inserts (see, e.g., Mejia (1997) Genome Res 7:179-186; Ioannou (1994) Nat Genet 6:84-89). PACs are screened in much the same way as lambda libraries. See also Ashworth (1995) Analytical Biochem. 224:564-571; Gingrich (1996) Genomics 32:65-74.

Other cloning vehicles can also be used, for example, recombinant viruses; cosmids, plasmids or cDNAs; see, e.g., U.S. Patent No. 5,501,979; 5,288,641; 5,266,489.

These vectors can include marker genes, such as, e.g., luciferase and green fluorescent protein genes (see, e.g., Baker (1997) Nucleic Acids Res 25:1950-1956). Sequences, inserts, clones, vectors and the like can be isolated from natural sources, obtained from such sources as ATCC or GenBank libraries or commercial sources, or prepared by synthetic or recombinant methods.

Amplification of Nucleic Acids

Amplification using oligonucleotide primers can be used to generate or manipulate, e.g., subclone, genomic nucleic acids used in the methods of the invention, to incorporate label into immobilized or sample nucleic acids, to detect or measure levels of nucleic acids hybridized to an array, and the like. Amplification, typically with degenerate primers, is also useful for incorporating detectable probes (e.g., Cy5™- or Cy3™-cytosine conjugates) into nucleic acids representative of test or control genomic DNA to be used to hybridize to immobilized genomic DNA. Amplification can be used to quantify the amount of nucleic acid is in a sample, see, e.g., U.S. Pat. No. 6,294,338. The skilled artisan can select and design suitable oligonucleotide amplification primers. Amplification methods are also well known in the art, and include, e.g., polymerase chain reaction, PCR (PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y., ligase chain reaction (LCR) (see, e.g., Wu (1989) Genomics 4:560; Landegren (1988) Science 241:1077; Barringer (1990) Gene 89:117); transcription amplification (see, e.g., Kwoh (1989) Proc. Natl. Acad. Sci. USA 86:1173); and, self-sustained sequence replication (see, e.g., Guatelli (1990) Proc. Natl. Acad. Sci. USA 87:1874); Q Beta replicase amplification (see, e.g., Smith (1997) J. Clin. Microbiol. 35:1477-1491), automated Q-beta replicase amplification assay (see, e.g., Burg (1996) Mol. Cell. Probes 10:257-271) and other RNA polymerase mediated techniques, e.g., nucleic acid sequence based amplification, or, "NASBA," see, e.g., Birch (2001) Lett. Appl. Microbiol. 33:296-301; Greijer (2001) J. Virol. Methods 96:133-147. See also Berger (1987) Methods Enzymol. 152:307-316; Sambrook; Ausubel; U.S. Pat. Nos. 4,683,195 and 4,683,202.

Hybridizing Nucleic Acids

In practicing the methods of the invention, samples of nucleic acid, e.g., isolated, cloned or amplified genomic nucleic acid, are hybridized to immobilized nucleic acids. In alternative aspects, the hybridization and/or wash conditions are carried out under moderate to stringent conditions. An extensive guide to the hybridization of nucleic acids is found in, e.g., Sambrook Ausubel, Tijssen. Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. Exemplary stringent hybridization conditions for hybridization of complementary nucleic acids which have more than 100 complementary residues on an array comprise 42° C. using standard hybridization solutions (see, e.g., Sambrook), with the hybridization being carried out overnight. Exemplary highly stringent wash conditions can also comprise 0.15 M NaCl at 72° C. for about 15 minutes. Exemplary stringent wash conditions can also comprise a 0.2×SSC wash at 65° C. for 15 minutes (see, e.g., Sambrook). In one aspect, a high stringency wash is preceded by a medium or low stringency wash to remove background probe signal. An exemplary medium stringency wash for a duplex of, e.g., more than 100 nucleotides, comprises 1×SSC at 45° C. for 15 minutes. An exemplary low stringency wash for a duplex of, e.g., more than 100 nucleotides, can comprise 4×to 6×SSC at 40° C. for 15 minutes.

In alternative aspects, in practicing the array-based comparative hybridization (CGH) reactions of the invention, the fluorescent dyes Cy3™ and Cy5™ are used to differentially label nucleic acid fragments from two samples, e.g., nucleic acid generated from a control versus a test cell or tissue. Many commercial instruments are designed to accommodate to detection of these two dyes. To increase the stability of Cy5™, or fluors or other oxidation-sensitive compounds, antioxidants and free radical scavengers can be used in hybridization mixes, the hybridization and/or the wash solutions. Thus, Cy5™ signals are dramatically increased and longer hybridization times are possible. See co-pending U.S. patent application Ser. No. (USSN) 09/839,658, filed Apr. 19, 2001.

To further increase the hybridization sensitivity, hybridization can be carried out in a controlled, unsaturated humidity environment; thus, hybridization efficiency is significantly improved if the humidity is not saturated. See co-pending U.S. Ser. No. 09/839,658, filed Apr. 19, 2001. The hybridization efficiency can be improved if the humidity is dynamically controlled, i.e., if the humidity changes during hybridization. Array devices comprising housings and controls that allow the operator to control the humidity during pre-hybridization, hybridization, wash and/or detection stages can be used. The device can have detection, control and memory components to allow pre-programming of the humidity (and temperature and other parameters) during the entire procedural cycle, including pre-hybridization, hybridization, wash and detection steps. See co-pending U.S. Ser. No. 09/839,658, filed Apr. 19, 2001.

The methods of the invention can incorporate hybridization conditions comprising temperature fluctuation. Hybridization has much better efficiency in a changing temperature environment as compared to conditions where the temperature is set precisely or at relatively constant level (e.g., plus or minus a couple of degrees, as with most commercial ovens). Reaction chamber temperatures can be fluctuatingly modified by, e.g., an oven, or other device capable of creating changing temperatures. See co-pending U.S. Ser. No. Apr. 19, 2001.

The methods of the invention can comprise hybridization conditions comprising osmotic fluctuation. Hybridization efficiency (i.e., time to equilibrium) can also be enhanced by a hybridization environment that comprises changing hyper-/ hypo-tonicity, e.g., a solute gradient. A solute gradient is created in the device. For example, a low salt hybridization solution is placed on one side of the array hybridization chamber and a higher salt buffer is placed on the other side to generate a solute gradient in the chamber. See co-pending U.S. Ser. No. 09/839,658, filed Apr. 19, 2001.

Fragmentation and Digestion of Nucleic Acid

In practicing the methods of the invention, immobilized and sample nucleic acids can be cloned, labeled or immobilized in a variety of lengths. For example, in one aspect, the genomic nucleic acid can have a length smaller than about 200 bases. Use of labeled genomic DNA limited to this small size significantly improves the resolution of the molecular profile analysis, e.g., in array-based CGH. For example, use of such small fragments allows for significant suppression of repetitive sequences and other unwanted, "background" cross-hybridization on the immobilized nucleic acid. Suppression of repetitive sequence hybridization greatly increases the reliability of the detection of copy number differences (e.g., amplifications or deletions) or detection of unique sequences. See co-pending U.S. Ser. No. 09/839,658, filed Apr. 19, 2001.

The resultant fragment lengths can be modified by, e.g., treatment with DNase. Adjusting the ratio of DNase to DNA polymerase in a nick translation reaction changes the length of the digestion product. Standard nick translation kits typically generate 300 to 600 base pair fragments. If desired, the labeled nucleic acid can be further fragmented to segments below 200 bases, down to as low as about 25 to 30 bases, random enzymatic digestion of the DNA is carried out, using, e.g., a DNA endonucleases, e.g., DNase (see, e.g., Herrera (1994) J. Mol. Biol. 236:405-411; Suck (1994) J. Mol. Recognit. 7:65-70), or, the two-base restriction endonuclease CviJI (see, e.g., Fitzgerald (1992) Nucleic Acids Res. 20:3753-3762) and standard protocols, see, e.g., Sambrook, Ausubel, with or without other fragmentation procedures.

Other procedures can also be used to fragment genomic DNA, e.g. mechanical shearing, sonication (see, e.g., Deininger (1983) Anal. Biochem. 129:216-223), and the like (see, e.g., Sambrook, Ausubel, Tijssen). For example, one mechanical technique is based on point-sink hydrodynamics that result when a DNA sample is forced through a small hole by a syringe pump, see, e.g., Thorstenson (1998) Genome Res. 8:848-855. See also, Oefner (1996) Nucleic Acids Res. 24:3879-3886; Ordahl (1976) Nucleic Acids Res. 3:2985-2999. Fragment size can be evaluated by a variety of techniques, including, e.g., sizing electrophoresis, as by Siles (1997) J. Chromatogr. A. 771:319-329, that analyzed DNA fragmentation using a dynamic size-sieving polymer solution in a capillary electrophoresis. Fragment sizes can also be determined by, e.g., matrix-assisted laser desorption/ionization time-of-flight mass spectrometry, see, e.g., Chiu (2000) Nucleic Acids Res. 28:E31.

Comparative Genomic Hybridization (CGH)

The methods of the invention are used in array-based comparative genomic hybridization (CGH) reactions to detect genetic mosaicism in cell populations, such as tissue, e.g., biopsy or body fluid samples. CGH is a molecular cytogenetics approach that can be used to detect regions in a genome undergoing quantitative changes, e.g., gains or losses of sequence or copy numbers. Analysis of genomes of tumor cells can detect a region or regions of anomaly undergoing gains and/or losses.

CGH reactions compare the genetic composition of test versus controls samples; e.g., whether a test sample of genomic DNA (e.g., from a cell population suspected of having one or more subpopulations comprising different, or cumulative, genetic defects) has amplified or deleted or mutated segments, as compared to a "negative" control, e.g., "normal" or "wild type" genotype, or "positive" control, e.g., a known cancer cell or a cell with a known defect, e.g., a translocation or deletion or amplification or the like.

The methods of the invention can be practiced with all known methods and means and variations thereof for carrying out comparative genomic hybridization, see, e.g., U.S. Pat. Nos. 6,197,501; 6,159,685; 5,976,790; 5,965,362; 5,856,097; 5,830,645; 5,721,098; 5,665,549; 5,635,351; and, Diago (2001) American J. of Pathol. May;158(5):1623-1631;(Theillet (2001) Bull. Cancer 88:261-268; Werner (2001) Pharmacogenomics 2:25-36; Jain (2000) Pharmacogenomics 1:289-307.

Arrays, or "BioChips"

In one aspect, the methods of the invention detect genetic mosaicisms in cell populations by performing an array-based comparative genomic hybridization (CGH). The present invention can be practiced with any known "array," also referred to as a "microarray" or "DNA array" or "nucleic acid array" or "biochip," or variation thereof. Arrays are generically a plurality of "target elements," or "spots," each target element comprising a defined amount of one or more biological molecules, e.g., polypeptides, nucleic acid molecules, or probes, immobilized on a defined location on a substrate surface. Typically, the immobilized biological molecules are contacted with a sample for specific binding, e.g., hybridization, between molecules in the sample and the array. Immobilized nucleic acids can contain sequences from specific messages (e.g., as cDNA libraries) or genes (e.g., genomic libraries), including, e.g., substantially all or a subsection of a chromosome or substantially all of a genome, including a human genome. Other target elements can contain reference sequences, such as positive and negative controls, and the like. The target elements of the arrays may be arranged on the substrate surface at different sizes and different densities. Different target elements of the arrays can have the same molecular species, but, at different amounts, densities, sizes, labeled or unlabeled, and the like. The target element sizes and densities will depend upon a number of factors, such as the nature of the label (the immobilized molecule can also be labeled), the substrate support (it is solid, semi-solid, fibrous, capillary or porous), and the like. Each target element may comprise substantially the same nucleic acid sequences, or, a mixture of nucleic acids of different lengths and/or sequences. Thus, for example, a target element may contain more than one copy of a cloned piece of DNA, and each copy may be broken into fragments of different lengths, as described herein. The length and complexity of the nucleic acid fixed onto the array surface is not critical to the invention. The array can comprise nucleic acids immobilized on any substrate, e.g., a solid surface (e.g., nitrocellulose, glass, quartz, fused silica, plastics and the like). See, e.g., U.S. Pat. No. 6,063,338 describing multi-well platforms comprising cycloolefin polymers if fluorescence is to be measured. Arrays used in the methods of the invention can comprise housing comprising components for controlling humidity and temperature during the hybridization and wash reactions.

In practicing the methods of the invention, known arrays and methods of making and using arrays can be incorporated in whole or in part, or variations thereof, as described, for example, in U.S. Pat. Nos. 6,277,628; 6,277,489; 6,261,776; 6,258,606; 6,054,270; 6,048,695; 6,045,996; 6,022,963; 6,013,440; 5,965,452; 5,959,098; 5,856,174; 5,830,645; 5,770,456; 5,632,957; 5,556,752; 5,143,854; 5,807,522; 5,800,992; 5,744,305; 5,700,637; 5,556,752; 5,434,049; see also, e.g., WO 99/51773; WO 99/09217; WO 97/46313; WO 96/17958; see also, e.g., Johnston (1998) Curr. Biol. 8:R171-R174; Schummer (1997) Biotechniques 23:1087-1092; Kern (1997) Biotechniques 23:120-124; Solinas-Toldo (1997) Genes, Chromosomes & Cancer 20:399-407; Bowtell (1999) Nature Genetics Supp. 21:25-32. See also published U.S. patent applications Nos. 20010018642; 20010019827; 20010016322; 20010014449; 20010014448; 20010012537; 20010008765. The present invention can use any known array, e.g., GeneChips™, Affymetrix, Santa Clara, CA; SpectralChip™ Mouse BAC Arrays, SpectralChip™ Human BAC Arrays and Custom Arrays of Spectral Genomics, Houston, Texas, and their accompanying manufacturer's instructions.

Substrate Surfaces

The arrays used to practice the invention can have substrate surfaces of a rigid, semi-rigid or flexible material. The substrate surface can be flat or planar, be shaped as wells, raised regions, etched trenches, pores, beads, filaments, or the like. Substrates can be of any material upon which a "capture probe" can be directly or indirectly bound. For example, suitable materials can include paper, glass (see, e.g., U.S. Pat. No. 5,843,767), ceramics, quartz or other crystalline substrates (e.g. gallium arsenide), metals, metalloids, polacryloylmorpholide, various plastics and plastic copolymers, Nylon™, Teflon™, polyethylene, polypropylene, poly(4-methylbutene), polystyrene, polystyrene/latex, polymethacrylate, poly(ethylene terephthalate), rayon, nylon, poly(vinyl butyrate), polyvinylidene difluoride (PVDF) (see, e.g., U.S. Pat. No. 6,024,872), silicones (see, e.g., U.S. Pat. No. 6,096,817), polyformaldehyde (see, e.g., U.S. Pat. Nos. 4,355,153; 4,652,613), cellulose (see, e.g., U.S. Pat. No. 5,068,269), cellulose acetate (see, e.g., U.S. Pat. No. 6,048,457), nitrocellulose, various membranes and gels (e.g., silica aerogels, see, e.g., U.S. Pat. No. 5,795,557), paramagnetic or superparamagnetic microparticles (see, e.g., U.S. Pat. No. 5,939,261) and the like. Reactive functional groups can be, e.g., hydroxyl, carboxyl, amino groups or the like. Silane (e.g., mono- and dihydroxyalkylsilanes, aminoalkyltrialkoxysilanes, 3-aminopropyl-triethoxysilane, 3-aminopropyltrimethoxysilane) can provide a hydroxyl functional group for reaction with an amine functional group.

Nucleic Acids and Detectable Moieties: Incorporating Labels and Scanning Arrays

The methods of the invention use nucleic acids associated with a detectable label, e.g., have incorporated or have been conjugated to a detectable moiety. Any detectable moiety can be used. The association with the detectable moiety can be covalent or non-covalent. In another aspect, the array-immobilized nucleic acids and sample nucleic acids are differentially detectable, e.g., they have different labels and emit difference signals.

Useful labels include, e.g., $^{32}P$, $^{35}S$, $^{3}H$, $^{14}C$, $^{125}I$, $^{131}I$; fluorescent dyes (e.g., Cy5™, Cy3™, FITC, rhodamine, lanthanide phosphors, Texas red), electron-dense reagents (e.g. gold), enzymes, e.g., as commonly used in an ELISA (e.g., horseradish peroxidase, beta-galactosidase, luciferase, alkaline phosphatase), colorimetric labels (e.g. colloidal gold), magnetic labels (e.g. Dynabeads™), biotin, dioxigenin, or haptens and proteins for which antisera or monoclonal antibodies are available. The label can be directly incorporated into the nucleic acid to be detected, or it can be attached to a probe or antibody that hybridizes or binds to the target. A peptide can be made detectable by incorporating (e.g., into a nucleoside base) predetermined polypeptide epitopes recognized by a secondary reporter (e.g., leucine zipper pair sequences, binding sites for secondary antibodies, transcriptional activator polypeptide, metal binding domains, epitope tags). Label can be attached by spacer arms of various lengths to reduce potential steric hindrance or impact on other useful or desired properties. See, e.g., Mansfield (1995) Mol Cell Probes 9:145-156. In array-based CGH, fluors can be paired together; for example, one fluor labeling the control (e.g., the "nucleic acid of "known, or normal, karyotype") and another fluor the test nucleic acid (e.g., from a chorionic villus sample or a cancer cell sample). Exemplary pairs are: rhodamine and fluorescein (see, e.g., DeRisi (1996) Nature Genetics 14:458-460); lissamine-conjugated nucleic acid analogs and fluorescein-conjugated nucleotide analogs (see, e.g., Shalon (1996) supra); Spectrum Red™ and Spectrum Green™ (Vysis, Downers Grove, Ill.); Cy3™ and Cy5™. Cy3™ and Cy5™ can be used together; both are fluorescent cyanine dyes produced by Amersham Life Sciences (Arlington Heights, Ill.). Cyanine and related dyes, such as merocyanine, styryl and oxonol dyes, are particularly strongly light-absorbing and highly luminescent, see, e.g., U.S. Pat. Nos. 4,337,063; 4,404,289; 6,048,982.

Other fluorescent nucleotide analogs can be used, see, e.g., Jameson (1997) Methods Enzymol. 278:363-390; Zhu (1994) Nucleic Acids Res. 22:3418-3422. U.S. Pat. Nos. 5,652,099 and 6,268,132 also describe nucleoside analogs for incorporation into nucleic acids, e.g., DNA and/or RNA, or oligonucleotides, via either enzymatic or chemical synthesis to produce fluorescent oligonucleotides. U.S. Pat. No. 5,135,717 describes phthalocyanine and tetrabenztriazaporphyrin reagents for use as fluorescent labels.

Detectable moieties can be incorporated into genomic nucleic acid and, if desired, "target" nucleic acid, by covalent or non-covalent means, e.g., by transcription, such as by random-primer labeling using Klenow polymerase, or "nick translation," or, amplification, or equivalent. For example, in one aspect, a nucleoside base is conjugated to a detectable moiety, such as a fluorescent dye, e.g., Cy3™ or Cy5™, and then incorporated into a sample genomic nucleic acid. Samples of genomic DNA can be incorporated with Cy3™- or Cy5™-dCTP conjugates mixed with unlabeled dCTP. Cy5™ is typically excited by the 633 nm line of HeNe laser, and emission is collected at 680 nm. See also, e.g., Bartosiewicz (2000) Archives of Biochem. Biophysics 376:66-73; Schena (1996) Proc. Natl. Acad. Sci. USA 93:10614-10619; Pinkel (1998) Nature Genetics 20:207-211; Pollack (1999) Nature Genetics 23:41-46.

In another aspect, when using PCR or nick translation to label nucleic acids, modified nucleotides synthesized by coupling allylamine-dUTP to the succinimidyl-ester derivatives of the fluorescent dyes or haptenes (such as biotin or digoxigenin) are used; this method allows custom preparation of most common fluorescent nucleotides, see, e.g., Henegariu (2000) Nat. Biotechnol. 18:345-348.

In the methods of the invention, labeling with a detectable composition (labeling with a detectable moiety) also can include a nucleic acid attached to another biological molecule, such as a nucleic acid, e.g., a nucleic acid in the form of a stem-loop structure as a "molecular beacon" or an "aptamer beacon." Molecular beacons as detectable moieties are well known in the art; for example, Sokol (1998) Proc. Natl. Acad. Sci. USA 95:11538-11543, synthesized "molecular beacon" reporter oligodeoxynucleotides with matched fluorescent donor and acceptor chromophores on their 5' and 3' ends. In the absence of a complementary nucleic acid strand, the molecular beacon remains in a stem-loop conformation where fluorescence resonance energy transfer prevents signal emission. On hybridization with a complementary sequence, the stem-loop structure opens increasing the physical distance between the donor and acceptor moieties thereby reducing fluorescence resonance energy transfer and allowing a detectable signal to be emitted when the beacon is excited by light of the appropriate wavelength. See also, e.g., Antony (2001) Biochemistry 40:9387-9395, describing a molecular beacon comprised of a G-rich 18-mer triplex forming oligodeoxyribonucleotide. See also U.S. Pat. Nos. 6,277,581 and 6,235,504.

Aptamer beacons are similar to molecular beacons; see, e.g., Hamaguchi (2001) Anal. Biochem. 294:126-131; Poddar (2001) Mol. Cell. Probes 15:161-167; Kaboev (2000) Nucleic Acids Res. 28:E94. Aptamer beacons can adopt two or more conformations, one of which allows ligand binding. A fluorescence-quenching pair is used to report changes in conformation induced by ligand binding. See also, e.g., Yamamoto (2000) Genes Cells 5:389-396; Smirnov (2000) Biochemistry 39:1462-1468.

In addition to methods for labeling nucleic acids with fluorescent dyes, methods for the simultaneous detection of multiple fluorophores are well known in the art, see, e.g., U.S. Pat. Nos. 5,539,517; 6,049,380; 6,054,279; 6,055,325. For example a spectrograph can image an emission spectrum onto a two-dimensional array of light detectors; a full spectrally resolved image of the array is thus obtained. Photophysics of the fluorophore, e.g., fluorescence quantum yield and photodestruction yield, and the sensitivity of the detector are read time parameters for an oligonucleotide array. With sufficient laser power and use of Cy5™ and/or Cy3™, which have lower photodestruction yields an array can be read in less than 5 seconds.

When using two or more fluors together (e.g., as in a CGH), such as Cy3™ and Cy5™, it is necessary to create a composite image of all the fluors. To acquire the two or more images, the array can be scanned either simultaneously or sequentially. Charge-coupled devices, or CCDs, are used in microarray scanning systems, including practicing the methods of the invention. Thus, CCDs used in the methods of the invention can scan and analyze multicolor fluorescence images.

Any known device or method, or variation thereof, can be used or adapted to practice the methods of the invention, including array reading or "scanning" devices, such as scanning and analyzing multicolor fluorescence images; see, e.g., U.S. patent application Nos. 6,294,331; 6,261,776; 6,252,664; 6,191,425; 6,143,495; 6,140,044; 6,066,459; 5,943,129; 5,922,617; 5,880,473; 5,846,708; 5,790,727; and, the patents cited in the discussion of arrays, herein. See also published U.S. patent applications Nos. 20010018514; 20010007747.

The methods of the invention further comprise data analysis, which can include the steps of determining, e.g., fluorescent intensity as a function of substrate position, removing "outliers" (data deviating from a predetermined statistical distribution), or calculating the relative binding affinity of the targets from the remaining data. The resulting data can be displayed as an image with color in each region varying according to the light emission or binding affinity between targets and probes. See, e.g., U.S. Pat. Nos. 5,324,633; 5,863,504; 6,045,996. The invention can also incorporate a device for detecting a labeled marker on a sample located on a support, see, e.g., U.S. Pat. No. 5,578,832.

Sources of Genomic Nucleic Acid

The invention provides methods of detecting a genetic mosaicism in any sample comprising nucleic acid, such as a cell population or tissue or fluid sample, by performing an array-based comparative genomic hybridization (CGH). The nucleic acid can be derived from (e.g., isolated from, amplified from, cloned from) genomic DNA. The genomic DNA can be from any source.

In one aspect, the cell, tissue or fluid sample from which the nucleic acid sample is prepared is taken from a patient suspected of having a pathology or a condition associated with genetic defects. The causality, diagnosis or prognosis of the pathology or condition may be associated with genetic defects, e.g., a cancer or tumor comprising cells with genomic nucleic acid base substitutions, amplifications, deletions and/or translocations. The cell, tissue or fluid can be from, e.g., amniotic samples, chorionic villus samples (CVS), serum, blood, chord (blood or urine samples, CSF or bone marrow aspirations, fecal samples, saliva, tears, tissue and surgical biopsies, needle or punch biopsies, and the like.

Methods of isolating cell, tissue or fluid samples are well known to those of skill in the art and include, but are not limited to, aspirations, tissue sections, drawing of blood or other fluids, surgical or needle biopsies, and the like. A "clinical sample" derived from a patient includes frozen sections or paraffin sections taken for histological purposes. The sample can also be derived from supernatants (of cell cultures), lysates of cells, cells from tissue culture in which it may be desirable to detect levels of mosaicisms, including chromosomal abnormalities and copy numbers.

Conditions Diagnosed by Detection of Genetic Mosaicism

The methods of the invention can be used for diagnosing diseases and conditions, formulating appropriate treatment plans and estimating a prognosis. The methods of the invention can be used in situations where the causality, diagnosis or prognosis of the pathology or condition is associated with one or more genetic defects, e.g., a cancer or tumor comprising cells with genomic nucleic acid base substitutions, amplifications, deletions and/or translocations, or, an inherited condition. In some situations, the amount or degree of different subpopulations comprising different genetic makeups (karyotypes) in a tumor or other cancer cell population from a patient can be helpful in classifying the cancer or formulating a treatment plan or prognosis. A high degree of genetic mosaicism in a cell population can be an indicator that a cancer is fast growing or is likely to metastasize. For example, a complex aberrant karyotype and possibly generation of transcription factors by fusion proteins was proposed to be a reason for the impaired mRNA expression of a tumor-suppressor gene in glioma-derived cell line, see Krex (2001) J. Neurooncol. 52:119-128.

Chromosome abnormalities are common causes of congenital malformations and spontaneous abortions. They include structural abnormalities, polyploidy, trisomy, and mosaicism. Very few autosomal trisomies survive to birth, the three most common being those for chromosome 13, 18 and 21 giving rise to the syndromes named Patau, Edward's and Down's respectively (see, e.g., Moore (2000) Eur. J. Hum. Genet. 8:223-228). Thus, in alternative aspects, the methods of the invention are used to diagnose Patau Syndrome, Edward's Syndrome and Down's Syndrome. See, e.g., Djalali (2000) Prenat. Diagn. 20:934-935. In alternative aspects, the methods of the invention are used to diagnose the following syndromes (Table 1):

TABLE 1

Chromosome Loci Profiles of Contiguous Gene Syndromes

| Chromosome number | Locus | Syndrome |
|---|---|---|
| 1 | 1p36 | 1p Deletion Syndrome |
| 3 | 3p25 - pter | 3p Deletion Syndrome |
| 3 | 3p21 - pter | 3p Duplication Syndrome |
| 4 | 4p16.3 | Wolf-Hirschhorn Syndrome |
| 4 | 4p15.2 - 16.1 | 4p Duplication Syndrome |
| 5 | 5p15.2 - pter | Cri du Chat Syndrome |
| 7 | 7p13.3 | Miller-Dieker Syndrome |
| 7 | 711.23 | William's Syndrome |
| 8 | 8q24.1 | Langer-Giedion Syndrome (LGS) |
| 8 | 8q24.1 | Trichorhinophalangeal Syndrome (TRPS) |
| 9 | 9p, usually 9p22 - pter | 9p Deletion Syndrome |
| 10 | 10p13p14 | DiGeorge Syndrome II |
| 11 | 11p13 | WAGR Syndrome |
| 11 | 11p15.5 | Beckwith-Wiedemann Syndrome |
| 11 | 11p11.2 | Potocki-Shaffer Syndrome (Multiple Exostoses II Locus) |
| 15 | 15q12 | Angelman Syndrome |
| 15 | 15q12 | Prader-Willi Syndrome |
| 16 | Distal 16p13.3 | Rubinstein-Taybi Syndrome |
| 17 | 17p12 | Charcot-Marie-Tooth Disease Type 1A(CMT-1A) |
| 17 | 17p12 | Hereditary Neuropathy with Liability to Pressure Palsies |
| 17 | 17p13.3 | Miller-Dieker Syndrome/Isolated Lissencephaly |
| 17 | 17p11.2 | Smith-Magenis Syndrome |
| 20 | 20p11.2p12 | Alagille Syndrome |
| 22 | 22q11.2 (also see 1-p13p14) | Digeoege/Velocardiofacial Syndrome |
| X | Xp21 | Adrenal Hypoplasia Congenita (AHC) |
| X | Xp21 | Duchenne/Becker Muscular Dystrophy |
| X | Xp21 | Glycerol Kinase Deficiency |
| X | Xp22 | Pelizaeus-Merzbacher Disease |
| X | Xp22.3 | Steroid Sulfatase Deficiency |
| Y | SRY locus/Yp | Abnormalities of the SRY locus |

Methods of the invention can also be used to detect aneuploidy of chromosomes 13, 18, 21, X, and Y from genomic DNA from newborn uncultured blood samples (see, e.g., Jalal (1997) Mayo Clin. Proc. 72:705-710). Mosaicism has been reported to occur in approximately 1%-2% of viable pregnancies studied by chorionic villus sampling at 9-11 weeks of gestation. It has been detected in pregnancies with both diploid and trisomic fetuses and appears to have an important effect on the intrauterine fetal survival, see, e.g., Harrison (1993) Hum. Genet. 92:353-358.

In in vitro fertilization (IVF) programs, preimplantation genetic diagnosis (PGD) of oocytes and embryos has become the technique of choice to select against abnormal embryos before embryo transfer. Thus, in alternative aspects, the methods of the invention are used for preimplantation genetic diagnosis and the diagnosis of structural abnormalities in oocytes and embryos. See, e.g., Fung (2001) J. Histochem. Cytochem. 49:797-798. Thus, in alternative aspects, the methods of the invention are used with chorionic villus sampling (CVS) and fetal karyotyping. See, e.g., Sanz (2001) Fetal Diagn. Ther. 16:95-97.

Genetic mosaicism is frequent among transgenic animals produced by pronuclear microinjection. A successful method for the screening of founder animals for germline mosaicism prior to mating would greatly reduce the costs associated with the propagation of the transgenic lines, and improve the efficiency of transgenic livestock production. Thus, in alternative aspects, the methods of the invention are used in the production of transgenic animals, particularly, the screening of founder animals for germline mosaicism prior to mating. See, e.g., Ibanez (2001) Mol. Reprod. Dev. 58:166-172.

EXAMPLES

The following example is offered to illustrate, but not to limit the claimed invention.

Example 1

Making Nucleic Acid Arrays

The following example demonstrates exemplary protocol for making an array of the invention.

Making BAC Microarrays:

BAC clones greater than fifty kilobases (50 kb), and up to about 300 kb, are grown up in Terrific Broth medium. Larger inserts, e.g., clones >300 kb, and smaller inserts, about 1 to 20 kb, are also be used. DNA is prepared by a modified alkaline lysis protocol (see, e.g., Sambrook). The DNA is labeled, as described below.

The DNA is then chemically modified as described by U.S. Pat. No. 6,048,695. The modified DNA is then dissolved in proper buffer and printed directly on clean glass surfaces as described by U.S. Pat. No. 6,048,695. Usually multiple spots are printed for each clone.

Example 2

Nucleic Acid Labeling and DNase Enzyme Fragmentation

A standard random priming method is used to label genomic DNA before its attachment to the array, see, e.g., Sambrook. Sample nucleic acid is also similarly labeled. Cy3™ or Cy5™ labeled nucleotides are supplemented together with corresponding unlabeled nucleotides at a molar ratio ranging from 0.0 to about 6 (unlabeled nucleotide to labeled nucleotides). Labeling is carried out at 37° C. for 2 to 10 hours. After labeling the reaction mix is heated up to 95° C. to 100° C. for 3 to 5 minutes to inactivate the polymerase and denature the newly generated, labeled "probe" nucleic acid from the template.

The heated sample is then chilled on ice for 5 minutes. "Calibrated" DNase (DNA endonuclease) enzyme is added to fragment the labeled template (generated by random priming). "Trace" amounts of DNase is added (final concentration was 0.2 to 2 ng/ml; incubation time 15 to 30 minutes) to digest/ fragment the labeled nucleic acid to segments of about 30 to about 100 bases in size.

A number of embodiments of the invention have been described. Nevertheless, it will be understood that various modifications may be made without departing from the spirit and scope of the invention. Accordingly, other embodiments are within the scope of the following claims.

What is claimed is:

1. A method of detecting a degree of genetic mosaicism in a cell population by performing an array-based comparative genomic hybridization (CGH), wherein an array comprising a plurality of cloned genomic nucleic acid segments is provided in a plurality of identical replicas, each cloned segment immobilized to a discrete and known spot on a substrate surface to form the array, the cloned genomic nucleic acid segments comprising a substantially complete first genome of a known first karyotype, the method comprising:
   (a) contacting replicas of the array with mixtures of a first nucleic acid sample and a second nucleic acid sample and fractional dilutions of the second sample, wherein the first sample comprises a plurality of genomic nucleic acid segments comprising a substantially complete complement of the first genome labeled with a first detectable label, the second sample-comprises a plurality of genomic nucleic acid segments comprising a substantially complete complement of the second genome labeled with a second detectable label, and the karyotype of the second sample is known and is different from that of the first sample;
   (b) contacting further replicas of the array with mixtures of the first nucleic acid sample and a third nucleic acid sample and fractional dilutions of the third sample, wherein the third sample comprises a genomic nucleic acid sample with an unknown karyotype and is labeled with the second detectable label, and the genomic nucleic acid of the third sample comprises a substantially complete complement of genomic nucleic acid of a third genome from a test cell or a tissue sample, wherein the contacting is under conditions wherein the nucleic acid in the mixtures of each of the first and second samples and the first and third samples can specifically hybridize to the genomic nucleic acid segments immobilized on the array;
   (c) measuring the amount of first label and second label on each spot for each respective contacted array and determining the karyotype of each dilution fraction by comparative genomic hybridization; and,
   (d) selecting which fractional dilution karyotype determination of the second sample most closely determines the known karyotype, and selecting data for the same fractional dilution of the third sample to determine the karyotype of the third sample, thereby determining the degree of genetic mosaicism in the-cell population.

2. The method of claim 1, wherein the cell population comprises human cells.

3. The method of claim 1, wherein the cell population is derived from an individual suspected of having a chromosomal abnormality.

4. The method of claim 1, wherein the cell population is selected from the group of samples of a body fluid; a tissue; a biopsy; a blood sample; an amniotic fluid; a chorionic villus sample; an embryonic cell; and an embryonic tissue.

5. The method of claim 4, wherein the body fluid or tissue sample comprises a cancer cell or a tumor cell sample.

6. The method of claim 1, wherein at least one of the first, second and third genomes comprises a mammalian genome.

7. The method of claim 6, wherein the first, second and third mammalian genomes comprise human genomes.

8. The method of claim 1, wherein a cloned nucleic acid segment is cloned in a construct comprising an artificial chromosome.

9. The method of claim 8, wherein the artificial chromosome comprises a bacterial artificial chromosome (BAC).

10. The method of claim 8, wherein the artificial chromosome is selected from the group consisting of a human artificial chromosome (HAC), a yeast artificial chromosome (YAC), a transformation-competent artificial chromosome (TAC), and a bacteriophage P1-derived artificial chromosome (PAC).

11. The method of claim 1, wherein a cloned nucleic acid segment is cloned in a construct comprising a vector selected from the group consisting of a cosmid vector, a plasmid vector and a viral vector.

12. The method of claim 8, wherein the cloned nucleic acid segment is between about 50 kilobases to about 500 kilobases in length.

13. The method of claim 12, wherein the cloned nucleic acid segment is between about 100 kilobases to about 400 kilobases in length.

14. The method of claim 13, wherein the cloned nucleic acid segment is about 300 kilobases in length.

15. The method of claim 1, wherein the karyotype of at least one of the first genome and the second genome is determined by conventional G-banding analysis, FISH or SKY.

16. The method of claim 1, wherein the detectable label comprises a fluorescent label.

17. The method of claim 16, wherein the fluorescent label comprises Cy5™ or equivalent.

18. The method of claim 16, wherein the fluorescent label comprises Cy3™ or equivalent.

19. The method of claim 16, wherein the fluorescent label comprises a rhodamine, a fluorescein or an aryl-substituted 4,4-difluoro-4-bora-3a, 4a-diaza-s-indacene dye or equivalents.

20. The method of claim 1, wherein the array-immobilized genome comprises a wild type genome.

21. The method of claim 20, wherein the first sample comprises a wild type genome.

22. The method of claim 1, wherein the second sample comprises a cancer cell population.

23. The method of claim 1, wherein the second sample comprises a mosaic karyotype.

24. The method of claim 23, wherein the second sample comprises a mosaic karyotype comprising two or more cell subpopulations, wherein each subpopulation comprises a different karyotype.

25. The method of claim 1, wherein the array-immobilized genomic nucleic acid segments in a first spot are non-overlapping in sequence compared to the array-immobilized genomic nucleic acid segments in a second spot.

26. The array of claim 25, wherein the array-immobilized genomic nucleic acid segments in a spot are non-overlapping in sequence compared to the array-immobilized genomic nucleic acid segments all of other genomic nucleic acid-comprising spots on the array.

27. The method of claim 1, wherein each cloned genomic nucleic acid segment is spotted in duplicate on the array.

28. The method of claim 1, wherein the array-immobilized genomic nucleic acid are covalently bound to the substrate surface.

29. The method of claim 28, wherein the array-immobilized genomic nucleic acid are covalently bound to a compound having the general formula: $R_1$—X—$R_2$, wherein $R_1$ is a cyclic ether; an aldehyde, or a chloromethylphenyl moiety; X is a moiety chemically suitable for linking the $R_1$ moiety to the $R_2$ moiety, and the $R_2$ moiety has the general formula

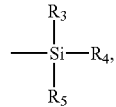

wherein $R_3$, $R_4$ and $R_5$ comprise identical or different alkoxy group or chioro groups.

30. The method of claim 1, wherein the array-immobilized genomic nucleic acid are covalently bound to a compound having the general formula: $R_1$—X—$R_2$, wherein $R_1$ is an amino group, $R_2$ is an alkoxysilane group or a chlorohalide group; and X is a moiety chemically suitable for linking the $R_1$ group and the $R_2$ group.

31. The method of claim 1, wherein the array-immobilized genomic nucleic acid are covalently bound to a compound having the general formula

wherein m+k is the integer 3, and n can be 0 if m is greater than 0, or n+k is the integer 3 and m can be 0 if n is greater than 0; X is an inert linker; $R_1$ comprises a group reactive toward the biological molecule; R is an alkyl group; and, $R_2$ is an alkyl group.

32. The method of claim 1, comprising use of a device that can measure which detectable labels are on which spots on the substrate surface.

33. The method of claim 32, wherein the device comprises a charge-coupled device (CCD).

34. The method of claim 33, wherein the device is capable of multicolor fluorescence imaging.

35. The method of claim 1, comprising use of a computer processor to analyze multicolor fluorescence imaging data.

36. The method of claim 1, further comprising use of a computer and a computer program algorithm to interpret data imaged from the array and display results of a karyotype analysis.

37. The method of claim 1, further comprising contacting the fractions of the sample under varying conditions.

38. The method of claim 37, wherein varying the conditions comprises varying a condition selected from temperature used in hybridization conditions; temperature used in wash conditions for each fraction; osmolarity of a hybridization buffer; osmolarity of a wash buffer; time each fraction is contacted; time before each fraction is washed; time during which each fraction is washed; humidity of the hybridization conditions; time each fraction is contacted to the array before reading; concentration of the nucleic acid; and size of the nucleic acid.

39. The method of claim 1, wherein said cell population is derived from an individual suspected of having a disease or condition associated with a karyotype abnormality.

40. The method of claim 39, wherein the disease or condition comprises a cancer.

* * * * *